United States Patent
Norlien

Patent Number: 5,357,972
Date of Patent: Oct. 25, 1994

[54] DISPOSABLE PNEUMOTACHOGRAPH FLOWMETER

[75] Inventor: John A. Norlien, Pine Springs, Minn.

[73] Assignee: Medical Graphics Corporation, St. Paul, Minn.

[21] Appl. No.: 61,230

[22] Filed: May 17, 1993

[51] Int. Cl.$^5$ ............................................. A61B 5/08
[52] U.S. Cl. ................................ 128/725; 73/272 R; 73/861.52
[58] Field of Search ............... 128/725, 719; 165/119; 73/279, 272 R, 861.52, 861.47

[56] References Cited

U.S. PATENT DOCUMENTS

| | | | |
|---|---|---|---|
| 3,626,755 | 12/1971 | Rudolph | 128/725 X |
| 3,718,135 | 2/1973 | Diamond et al. | 128/725 |
| 4,178,919 | 12/1979 | Hall | 128/719 |
| 4,368,740 | 1/1983 | Binder | 128/718 |
| 4,440,177 | 4/1984 | Anderson et al. | 128/719 |
| 4,995,400 | 2/1991 | Boehringer et al. | 128/725 |
| 5,033,312 | 7/1991 | Stupecky | 73/861.53 |
| 5,058,601 | 10/1991 | Riker | 128/725 |
| 5,060,655 | 10/1991 | Rudolph | 128/716 |
| 5,111,827 | 5/1992 | Rantala | 128/719 |
| 5,137,026 | 8/1992 | Waterson et al. | 128/725 |

FOREIGN PATENT DOCUMENTS

| | | | |
|---|---|---|---|
| 331772 | 9/1989 | European Pat. Off. | 128/725 |
| 373886 | 6/1990 | European Pat. Off. | 128/725 |

OTHER PUBLICATIONS

"Flow Meter for Recording Respiratory Flow of Human Subjects", by John C. Lilly, Methods in Medical Research, vol. 2, 1950.

Primary Examiner—Edgar S. Burr
Assistant Examiner—Eric P. Raciti
Attorney, Agent, or Firm—Haugen and Nikolai

[57] ABSTRACT

A disposable pneumotachograph flowmeter comprises first and second tubular mouthpiece members which, when juxtaposed relative to one another, sandwich a fabric screen made from a hydrophobic material therebetween. The screen may comprise a woven fabric formed from expanded PTFE fibers or, alternatively, may be a non-woven mat of polyester fibers. Because of the properties of the screen material, it does not become clogged and occluded with moisture particles during use.

5 Claims, 1 Drawing Sheet

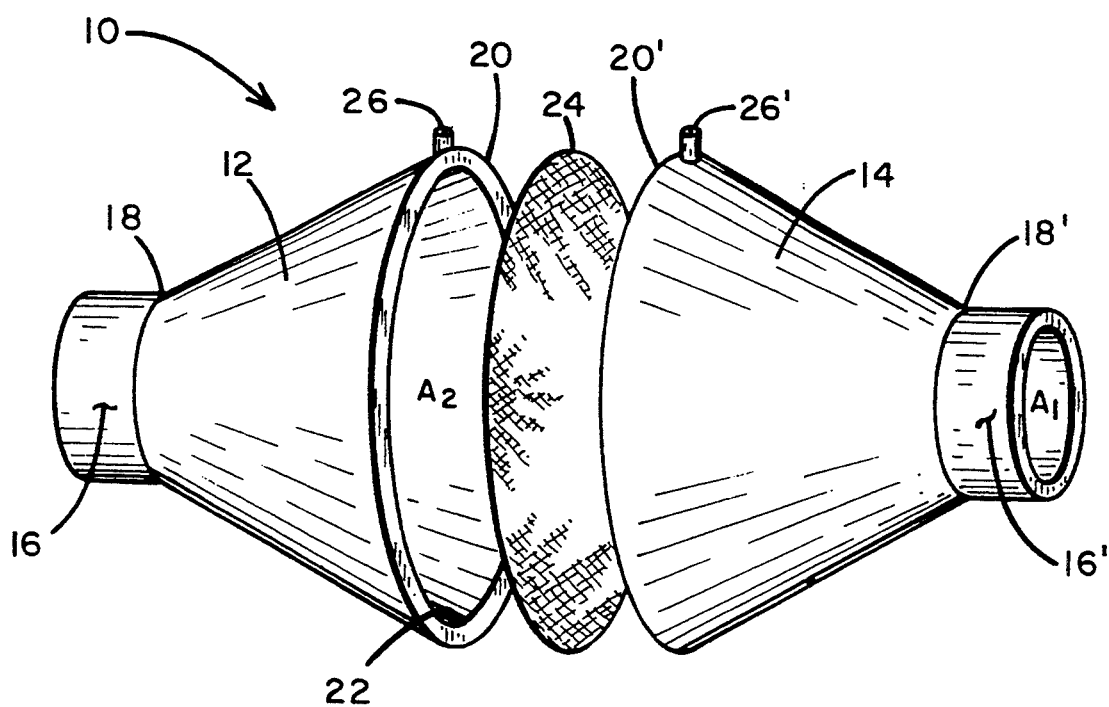

DISPOSABLE PNEUMOTACHOGRAPH FLOWMETER

BACKGROUND OF THE INVENTION

I. Field of the Invention

This invention relates generally to respiratory gas flow measuring devices, and more particularly to a low-cost, disposable pneumotachograph flowmeter incorporating a hydrophobic fabric screen to thereby obviate the need for a built-in heater commonly found in devices of this type.

II. Discussion of the Prior Art

Medical diagnostic equipment employed to assess pulmonary performance of a subject requires an accurate measurement of respiratory gas flow during inspiration and expiration. A device often used to accomplish this end is a pneumotachograph flowmeter. It is commonly referred to as a Fleisch flowmeter and is available through the Hans Rudolph Company of St. Louis, Mo. That device comprises a tubular housing having a metal screen extending transversely to the direction of fluid flow through the tubular housing. Pressure sensing ports pass through the wall of the tubular member on opposite sides of the metal screen. The pressure differential measured across the two ports during inspiration and expiration provide an indication of the fluid flow through the screen.

In that respiratory gas is heavily ladened with water vapor, it can condense and collect on the metal screen and thereby adversely impact the accuracy of the flow measurement. To counteract this problem, the Fleisch pneumotachograph incorporates one or more screens that are arranged to be electrically heated to a temperature that precludes condensation of water vapor thereon. However, the addition of the heating elements to the device necessarily increases its cost to the point where discarding it after a single use becomes prohibitive. This is true even though the cleaning and sterilization steps following use is a necessary cost consideration.

SUMMARY OF THE INVENTION

It is accordingly a principal object of the present invention to provide a low-cost, yet accurate, pneumotachograph flowmeter.

Another object of the invention is to provide a pneumotachograph flowmeter that does not require the use of heating elements for inhibiting the buildup of condensation on its screen member.

Still another object of the invention is to provide a pneumotachograph flowmeter which can be fabricated at such low cost that it can be economically disposed of after only a single use.

In accordance with the present invention, the pneumotachograph flowmeter comprises a tubular mouthpiece member having a lumen extending the length thereof and a fabric screen of a hydrophobic material with pores of an average size of about $2.25 \times 10^{-6}$ square inches, the screen extending transverse to the lumen of the mouthpiece and with pressure-sensing ports in the mouthpiece member located on opposite sides of the fabric screen. In accordance with one embodiment of the invention, the fabric screen may comprise woven, expanded PTFE fibers, where the pores defined by the fibers have an area in the range of from $2.0 \times 10^{-6}$ to $2.5 \times 10^{-6}$ square inches, thereby enhancing laminar flow of fluid through the fabric screen material and a more linear relationship between the measured pressure drop and flow. In accordance with an alternative embodiment, the screen may comprise a non-woven mat of polyester fibers, that material being sold under the trademark, TYVAC, by the DuPont Corporation of Wilmington, Del.

In fabricating the preferred embodiment, the tubular mouthpiece member may comprise first and second substantially identical pieces, each having a tubular segment of a first cross-sectional area and a second tubular segment having first and second ends where the first end is integrally joined to the first tubular segment and the second end has a second cross-sectional area greater than the first cross-sectional area. The two pieces are brought together on opposite sides of the fabric screen with the second ends thereof being juxtaposed. The pressure-sensing ports are formed through the wall of the first and second pieces proximate the second ends of each so that they are effectively separated by the fabric screen.

Because the fabric screen is made from a hydrophobic material, water vapor in the respiratory gases pass through the pores rather than collecting and condensing on it. For this reason, there is no need to provide heating elements in the instrument as has heretofore been required with prior art designs.

DESCRIPTION OF THE DRAWINGS

The foregoing features, objects and advantages of the invention will become apparent to those skilled in the art from the following detailed description of a preferred embodiment, especially when considered in conjunction with the accompanying drawing depicting an exploded view of the pneumotachograph flowmeter constructed in accordance with the present invention.

DESCRIPTION OF A PREFERRED EMBODIMENT

Referring to the drawing, there is indicated generally by numeral 10 a pneumotachograph flowmeter constructed in accordance with the present invention. It is seen to include first and second molded plastic tubular pieces 12 and 14 which are generally identical in their construction, with each including a first tubular segment 16–16' having a cross-sectional area $A_1$ and a second tubular segment having first and second ends 18–18' and 20–20'. The first end 18–18' is integrally joined to the first segment 16–16'. The second end 20–20' of the segments 12 and 14 each have a cross-sectional area $A_2$ that is greater than the first cross-sectional area $A_1$. In the drawing, the segments 12 and 14 are shown as being conical in shape, however, limitation to that configuration is not intended. The flared or tapered configuration of the lumen 22 reduces the flow velocity which tends to promote laminar fluid flow when the mouthpiece segment 16 is placed in the subject's mouth and respiratory gases are inhaled and exhaled. The resulting measurements are thus not influenced by a change in the shape of the patient's mouth. The mouthpiece members 12 and 14 may be molded or otherwise formed from a suitable plastic, such as an acrylic. Other plastic materials may be used as well. Sandwiched between the mouthpiece members 12 and 14 and extending transverse to the lumen 22 and therefore the direction of fluid flow, is a fabric "screen" 24. This screen is preferably formed as woven expanded PTFE fibers having a predetermined pore size. A suitable material for the screen 24 a PTFE fabric sold under the trademark, GORTEX, by W. L. Gore & Associates, Inc. This material is hydrophobic and, therefore, non-water absorbing. The mesh-size of the woven fabric comprising screen 24 preferably provides about 400 pores per inch, a value that permits a laminar flow of the respiratory gases therethrough. Such a screen does not impose an unacceptable resistance to the gas flow.

While a PTFE woven screen is preferred, it has also been determined that a non-woven mat of polyester fibers, such as is sold under the trademark, TYVAC, by the DuPont Corporation of Wilmington, Del., may also be used. This material is gas pervious and hydrophobic so that the intersticial pores extending through its thickness dimension do not become occluded by water droplets which may condense out from the respiratory gases passing through the flowmeter device 10.

When the device shown in the drawings is assembled, first and second pressure taps 26 and 26' extend through the wall defining the lumen 22 and on opposite sides of the intermediately located fabric screen member 24. The pressure taps include a radially projecting tubular stub, allowing same to be coupled by appropriate tubing to apparatus (not shown) for measuring the pressure drop or differential across the screen 24. As those skilled in the art appreciate, this pressure drop is directly proportional to the volume rate of flow of respiratory gases through the mouthpiece during inhalation and exhalation.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A pneumotachograph flowmeter comprising:
   (a) a tubular mouthpiece member having a lumen extending the length thereof;
   (b) a fabric screen of expanded, PTFE fibers extending transverse to said lumen and having a multiplicity of pores, the size providing a predetermined resistance to fluid flow therethrough with the flow being laminar through said lumen; and
   (c) pressure sensing ports in said mouthpiece member disposed on opposite sides of said screen.

2. The pneumotachograph flow member as in claim 1 wherein said pores are of a size on the order of $2.25 \times 10^{-6}$ square inches.

3. The pneumotachograph flowmeter as in claim 1 wherein said tubular mouthpiece member comprises:
   (a) a first piece having a tubular segment with a first cross-sectional area and a second tubular segment having first and second ends, said first end being integrally joined to said first segment and said second end having a second cross-sectional area greater than said first cross-sectional area;
   (b) a second piece having a tubular segment with a first cross-sectional area and second tubular segment having first and second ends, said first end being joined to said first segment and said second end having a second cross-sectional area equal to said second cross-sectional area of said second end of said first piece; and
   (c) said fabric screen being in covering relation to said second ends of said first and second pieces when said second ends of said first and second pieces are juxtaposed across said fabric screen.

4. The pneumotachograph flowmeter as in claim 3 wherein said pressure sensing ports are formed through a wall surface of said first and second pieces proximate said second ends of each.

5. A pneumotachograph flowmeter comprising:
   (a) a tubular mouthpiece member having a lumen extending the length thereof;
   (b) a fabric screen of a non-woven polyester fiber material having randomly located pores extending therethrough, with the average size of said pores being about $2.225 \times 10^{-6}$ square inches so as to offer a predetermined resistance to fluid flow with the flow being laminar through said lumen, and
   (c) pressure sensing ports in said mouthpiece member disposed on opposite sides of said screen.

* * * * *